(12) United States Patent
Starr

(10) Patent No.: US 10,946,152 B2
(45) Date of Patent: Mar. 16, 2021

(54) PC-BASED PHYSIOLOGIC MONITOR AND SYSTEM FOR RESOLVING APNEA EPISODES DURING SEDATION

(71) Applicant: KONINKLIJKE PHILIPS N.V., Eindhoven (NL)

(72) Inventor: Eric W. Starr, Allison Park, PA (US)

(73) Assignee: Koninklijke Philips N.V., Eindhoven (NL)

( * ) Notice: Subject to any disclaimer, the term of this patent is extended or adjusted under 35 U.S.C. 154(b) by 515 days.

(21) Appl. No.: 15/823,108

(22) Filed: Nov. 27, 2017

(65) Prior Publication Data

US 2018/0078720 A1 Mar. 22, 2018

Related U.S. Application Data

(63) Continuation of application No. 11/389,403, filed on Mar. 24, 2006, now abandoned.
(Continued)

(51) Int. Cl.
*A61M 16/01* (2006.01)
*A61M 16/10* (2006.01)
(Continued)

(52) U.S. Cl.
CPC .......... *A61M 16/01* (2013.01); *A61M 16/021* (2017.08); *A61M 16/104* (2013.01);
(Continued)

(58) Field of Classification Search
CPC .. A61M 16/01; A61M 16/021; A61M 16/022; A61M 16/024; A61M 16/026;
(Continued)

(56) References Cited

U.S. PATENT DOCUMENTS 4,016,557 A 4/1977 Zitelli et al.
4,032,784 A 6/1977 Rich
(Continued)

OTHER PUBLICATIONS

PCT Search Report and Written Opinion, dated Oct. 16, 2007.
(Continued)

*Primary Examiner* — Joseph D. Boecker
*Assistant Examiner* — Thomas W Greig
(74) *Attorney, Agent, or Firm* — Daniel H. Brean

(57) ABSTRACT

An anesthesia delivery and monitoring system for use during outpatient surgery performed under sedation level anesthesia that includes a ventilatory system, a system for supplying sedation anesthesia, a respiratory sensor adapted to detect a respiration parameter of such a patient, and a system for supplying a timed back-up breath to such a patient through the ventilatory system. The timed back-up breaths are supplied in response to the respiration parameter falling outside a preset threshold and at a positive pressure exceeding a base operating pressure of the respiratory system. The system for supplying sedation anesthesia is an intravenous supply system for anesthesia, a ventilatory system coupled to the patient, a needle and syringe, or any combination thereof. The respiratory system includes a PC-based physiologic monitor with user modified feedback control signal.

21 Claims, 3 Drawing Sheets

Related U.S. Application Data

(60) Provisional application No. 60/665,919, filed on Mar. 28, 2005.

(51) Int. Cl.
*A61M 16/00* (2006.01)
*A61B 5/087* (2006.01)
*A61B 5/00* (2006.01)
*A61M 5/172* (2006.01)

(52) U.S. Cl.
CPC ............ *A61B 5/087* (2013.01); *A61B 5/4818* (2013.01); *A61M 5/1723* (2013.01); *A61M 2230/04* (2013.01); *A61M 2230/40* (2013.01); *A61M 2230/63* (2013.01)

(58) Field of Classification Search
CPC ............ A61M 16/104; A61M 16/0069; A61B 5/4814; A61B 5/4818
See application file for complete search history.

(56) References Cited

U.S. PATENT DOCUMENTS

| | | | |
|---|---|---|---|
| 4,958,139 A | 9/1990 | Hyatt | |
| 5,005,142 A | 4/1991 | Lipchak et al. | |
| 5,157,348 A | 10/1992 | Deveau | |
| 5,259,373 A * | 11/1993 | Gruenke | A61M 16/026 128/204.23 |
| 5,503,146 A * | 4/1996 | Froehlich | A61M 16/024 128/202.22 |
| 5,551,419 A * | 9/1996 | Froehlich | A61M 16/024 128/204.23 |
| 5,692,497 A | 12/1997 | Schnitzer et al. | |
| 5,844,430 A | 12/1998 | Thurnau et al. | |
| 6,032,109 A | 2/2000 | Ritmiller | |
| 6,064,898 A | 5/2000 | Aldrich | |
| 6,123,072 A | 9/2000 | Downs | |
| 6,158,433 A * | 12/2000 | Ong | A61M 16/0051 128/204.18 |
| 6,159,147 A | 12/2000 | Lichter et al. | |
| 6,429,718 B1 | 8/2002 | Lauter et al. | |
| 6,448,914 B1 | 9/2002 | Younis et al. | |
| 6,457,472 B1 | 10/2002 | Schwartz et al. | |
| 6,473,008 B2 | 10/2002 | Kelly et al. | |
| 6,536,430 B1 | 3/2003 | Smith | |
| 6,560,976 B2 | 5/2003 | Jayanth | |
| 6,637,434 B2 | 10/2003 | Noble | |
| 6,740,046 B2 | 5/2004 | Knapp et al. | |
| 7,680,537 B2 * | 3/2010 | Stahmann | A61N 1/36514 607/42 |
| 7,758,503 B2 * | 7/2010 | Lynn | G06F 19/00 600/300 |
| 8,925,545 B2 * | 1/2015 | Wondka | A61M 16/10 128/204.23 |
| 2002/0077856 A1 * | 6/2002 | Pawlikowski | G16H 40/40 705/2 |
| 2003/0145854 A1 * | 8/2003 | Hickle | A61M 5/142 128/204.18 |
| 2019/0150789 A1 * | 5/2019 | Lynn | A61B 5/14551 |

OTHER PUBLICATIONS

Iwama, "Application of Nasal Bi-Level Positive Airway Pressure to Respiratory Support During Combined Epidural-Propofol Anesthesia", Journal of Clinical Anesthesia, 2002, pp. 24-33, 14:24, Elsevier Science, Inc., New York, NY, USA.

Keidan et al., "Work of Breathing During Spontaneous Ventilation in Anesthetized Children: A Comparative Study Among the Face Mask, Laryngeal Mask Airway and Endotracheal Tube", Anesth Analg, 2000, pp. 1381-1388, 91:13, Pittsburgh, PA, USA.

Napoli et al., "General Anesthesia with Spontaneous Ventilation Without Intubation for Short-Stay Operations", Sep. 2002, pp. 669-675, vol. 68, No. 9.

Obamed, Inc., OBA-1(R) and OBA-1(R)MRI Units product information, 2003, Louisville, Kentucky, USA.

* cited by examiner

PC-BASED PHYSIOLOGIC MONITOR AND SYSTEM FOR RESOLVING APNEA EPISODES DURING SEDATION

CROSS-REFERENCE TO RELATED APPLICATIONS

This application is a continuation of U.S. Ser. No. 11/389,403 filed Mar. 24, 2006 which claims priority under 35 U.S.C. § 119(e) from provisional U.S. patent application No. 60/665,919 filed Mar. 28, 2005, the contents of which are incorporated herein by reference.

BACKGROUND OF THE INVENTION

1. Field of the Invention

The present invention relates to resolving apnea episodes during sedentary anesthesia, and, in particular, to the use of a ventilator system that delivers timed back-up breaths to patients during sedentary anesthesia, and to a PC-based physiologic monitor used in such a system.

2. Description of the Related Art

During surgery and other procedures in which the patient undergoes a light plane of anesthesia, also called sedation level anesthesia or sedentary anesthesia, the patent is given anesthesia, but an artificial airway and mechanical ventilation is not utilized, which is a procedure done during a more major surgery using a general anesthesia. Because the airway is not protected and breathing is not assisted, the patient under sedation level anesthesia can experience obstructive apneas, as well as, hypoventilation and central apneas. Patients are also known to accidentally drift from a light plane of anesthesia to a deep plane. When this occurs, patients are known to experience obstructive apneas, hypopneas, hypoventilation, and central apneas.

It has been previously proposed to apply continuous positive airway pressure (CPAP) respiratory therapy to certain patients during certain levels of anesthesia to maintain the patency of the airway. Furthermore, it has been proposed to apply a bi-level pressure support therapy, in which the pressure of the flow of gas delivered to the patient varies with the patient's respiratory cycle, to certain patients during certain levels of anesthesia to maintain the patency of the airway and to ensure that the patient receives a desired tidal volume. These systems represent active additional respiratory therapies that are applied to certain patients without regard to whether the patient is actually in need of the therapy. That is, some patients are being given a CPAP or bi-level therapy even though that patient may not be experiencing apneas or hypopneas. There is a need in the art to provide a ventilatory system that is responsive to sensed patient conditions, particularly in sedentary anesthesia applications, and to provide such a system without requiring the use of complicated and costly anesthesia machines used by hospitals during general anesthesia.

SUMMARY OF THE INVENTION

Accordingly, it is an object of the present invention to provide a monitor system that overcomes the shortcomings of conventional techniques for monitoring a patient, especially during sedation level anesthesia. This object is achieved, according to one embodiment of the present invention, by providing a personal computer (PC) based physiologic monitor system that includes a personal computer having a display and an input/output port for attachment to an external device. The PC based system also includes a physiologic sensor coupled to the personal computer through the input/output port so that a modified output of the physiologic sensor is graphically displayed on the display. A controller, a portion of which is disposed in the personal computer, modifies the output of the physiologic sensor and provides a feedback control signal for modifying the output of the physiologic sensor.

It is a further object of the present invention to provide a ventilatory system for use during outpatient surgery performed under sedation level anesthesia that overcomes the shortcomings of conventional pressure support systems used in this environment. This object is achieved, according to one embodiment of the present invention, by providing a ventilatory system for use during outpatient surgery performed under sedation level anesthesia that includes a pressure/flow generating system adapted to be coupled to a patient, a system for supplying sedation anesthesia to such a patient, a sensor coupled to such a patient and adapted to detect a respiration parameter of such a patient, and a controller. The controller receives the output from the sensor and controls the pressure/flow generating system so as to provide a timed back-up breath to such a patient based on the output from the sensor. The timed back-up breath is supplied in response to the respiration parameter falling outside a preset threshold, and is supplied at a positive pressure exceeding a base operating pressure of the pressure/flow generating system.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
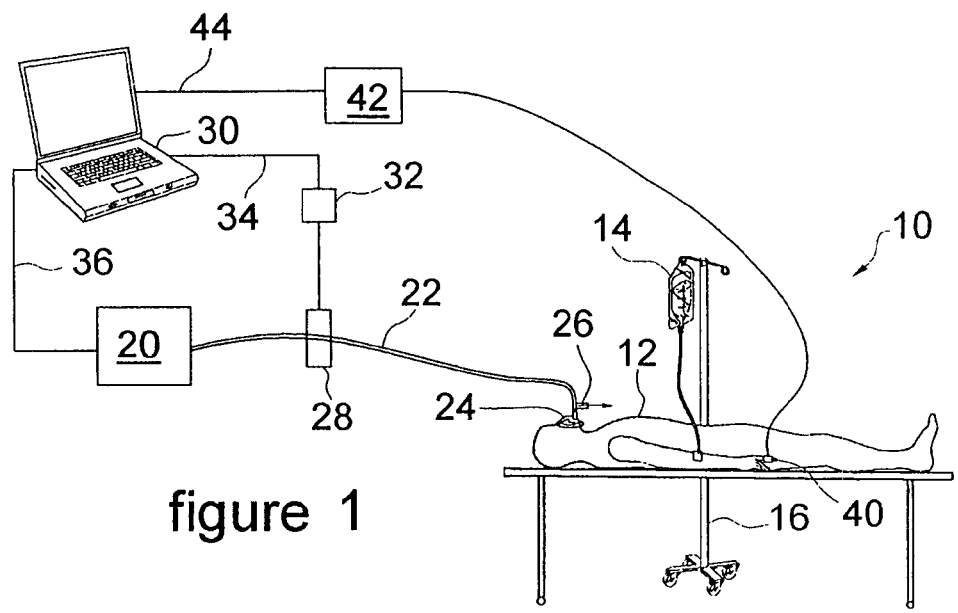
FIG. 1 is a schematic view of a first embodiment of a anesthesia delivery and monitoring system for use during outpatient surgery performed under sedation level anesthesia according to the principles of the present invention.
Figure 2:
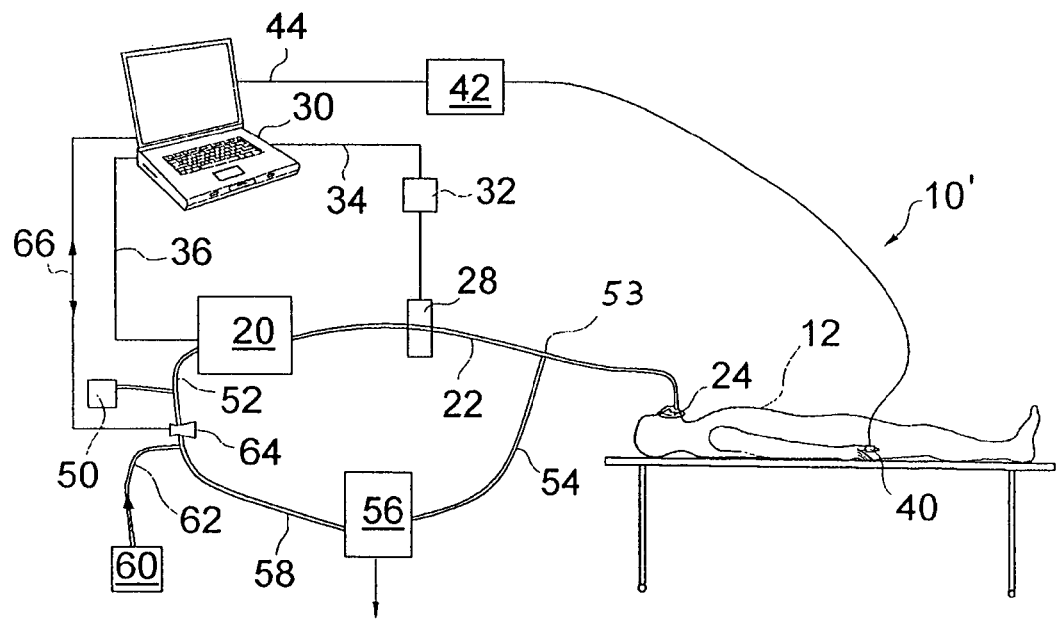
FIG. 2 is a schematic view of a second embodiment of a anesthesia delivery and monitoring system for use during outpatient surgery performed under sedation level anesthesia according to the principles of the present invention.

FIG. 1 is a schematic representation of a first embodiment of a anesthesia delivery and monitoring system 10 for use during outpatient surgery performed under sedation level anesthesia according to the principles of the present invention. As noted above, sedation level anesthesia refers to a level of anesthesia below general anesthesia, where a patient 12 is intended to be maintained in what is known as a light plane of anesthesia. This is common in many outpatient surgeries. The specific types of anesthesia utilized are well known in the art and are applied in a number of common techniques. Three common systems for supplying sedation anesthesia to patient 12 include: (1) an intravenous supply system for anesthesia, which is such as shown in FIG. 1; (2) an anesthesia/ventilatory system coupled to the patient, such as shown in FIG. 2, and (3) a needle and syringe injection (not shown). In the intravenous supply system of FIG. 1, the sedentary aesthesia is provided in an appropriate solution in an IV bag 14, which is mounted on a conventional stand 16. As noted above, a needle and syringe could also be used to supply intravenous sedentary anesthesia to patient 12 through simple, periodic injections.

Anesthesia delivery and monitoring system 10 of the present invention includes a ventilatory system coupled to a patient. Specifically, the ventilatory system includes a controlled pressure/flow generator 20, which is typically a blower having a respiratory gas intake and power supply (not shown) and a respiratory gas output, coupled to the patient 12 through a conduit 22 and a patient interface device 24. Patient interface device 24 is any conventional device that communicates a flow of gas from conduit 22 to an airway of a patient, such as a nasal mask, nasal/oral mask, nasal canula, or other respiratory patient coupling. Because conduit 22 is a single-limb conduit, patient interface device 24, conduit 22, or both includes an exhaust vent 26 for exhausting gas, such as a patient's exhaled breath, from the system to the ambient atmosphere, as generally known in the art. The present invention contemplates that the exhaust vent can be any suitable type of vent of expelling gas from the system to the atmosphere, conduit 22 can be any suitable conduit, such as a flexible hose, and pressure/flow generator 20 is any device capable of producing a flow of gas.

Anesthesia delivery and monitoring system 10 includes a sensor 28 coupled to patient 12 and adapted to detect a respiration parameter of the patient. In FIG. 1, sensor 28 is attached to patient 12 through conduit 22. In this configuration, sensor 28 may be a pressure sensor or flow sensor for detecting the respiration parameters of the patient. Sensor 28 could be placed on mask 24, at vent 26, on blower motor 20, or any combination thereof, and obtain signals indicative of the patient's respiration parameters. Sensor 28 may be placed directly on the patient 12 as well. The specific type and the location of the sensor can vary, provided that the sensor provides an output indicative of the patient's respiration parameters, i.e., at least the time of and preferably an indication of how much respiratory flow or volume the patient is receiving with each breath.

In anesthesia delivery and monitoring system 10, pressure/flow generator 20 and sensor 28 are coupled to a central controller that is in the form of a lap-top computer 30. In the illustrated exemplary embodiment, sensor 28 is coupled to computer 30 through an amplifier 32 to prove a meaningful signal to computer 30. Of course, amplifier 32 can be built into the sensor or the computer. The coupling between amplifier 32 and computer 30, shown as link 34, may be a hardwire connection or a wireless connection. In a similar fashion, the coupling between blower motor 20 and computer 30, shown as link 36, may be a hardwire connection or a wireless connection. Where links 34 are hardwire connections, it is preferred that they couple to conventional existing ports of laptop computer 30.

Anesthesia delivery and monitoring system 10 includes other physiologic sensors coupled to patient 12. Specifically, a pulse oximeter sensor 40 is attached to the patient and coupled to the computer through an amplifier 42 and link 44. The link between amplifier 42 and computer 30, shown discussed above, may also be a hardwire connection or a wireless connection. The addition of physiologic sensors, such as sensors 28 and 40, allows the computer to be a physiologic monitor graphically displaying the sensed parameters of the patient, as will be described in detail hereinafter. The sensors for this physiologic monitor are not limited to respiratory, pulse and blood oxygenation, as shown in FIGS. 1 and 2, but may further include a blood pressure sensor, a blood flow sensor, a blood glucose sensor, a blood cholesterol sensor, a heart sound sensor, an EMG sensor, an EEG sensor, an EKG sensor, an EOG sensor, a blood perfusion sensor, a temperature sensor, a blood gas sensor, a motion sensor, a strain gauge, a body position sensor, a limb motion sensor, and any combinations thereof.

Anesthesia delivery and monitoring system 10' of FIG. 2 is similar to system 10 of FIG. 1 except that system 10' includes a system for supplying sedation anesthesia to patient 12. Inhaled anesthesia agents are used in the embodiment of FIG. 2, which are supplied to pressure/flow generator 20 through an anesthesia gas supply 50 and an input conduit 52. When using inhaled agents for anesthesia, the ventilatory system cannot vent to the room, or it could adversely affect the caregivers. Therefore, a closed (dual limb) system is created where vent 26 is replaced with a one way T or Y coupling 53 and a expiratory limb 54 that carries the gas to a $CO_2$/anesthesia scrubber 56 that vents harmless material or returns the scrubbed respiratory gases to input 52 through tubing 58.

In the illustrated embodiment, a source of oxygen 60 is coupled to input conduit 52 through tubing 62 to supply oxygen to the closed system. An oxygen sensor 64 may be coupled to input conduit 52 (or elsewhere on the closed system) and coupled to controller 30 through a link 66. The link between sensor 64 (which may have an amplifier) and computer 30, may be a hardwire connection or a wireless connection. As a closed respiratory system, it is sometimes desirable to track the oxygen level received by the patient.

The operation of anesthesia delivery and monitoring systems 10 and 10' are used in the present invention in that the ventilatory portion of the system provides a system for supplying a timed back-up breath to the patient. More specifically, the timed back-up breaths are supplied in response to the respiration parameter falling outside a preset threshold. As noted above, timed back-up breaths, within the meaning of this disclosure, refer to the supplying of positive pressure to the airway of the patient to assist the patient's breathing. This is done in response to a sensed failure of the patient's actual breathing over a given period of time.

Figure 3:
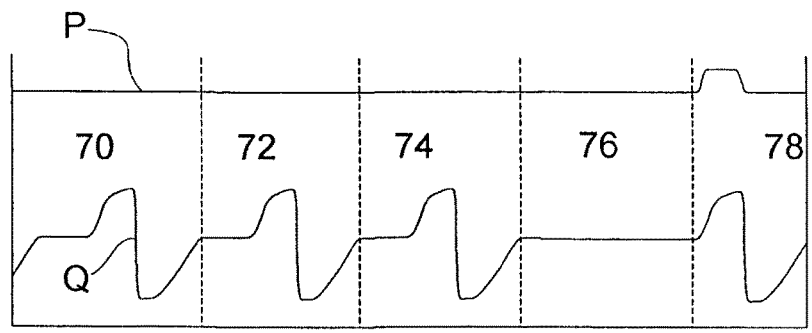
FIG. 3 is a schematic representation of the output pressure of the anesthesia delivery and monitoring system of the present invention and the patient's tidal volume displayed over a period of time.

Referring to FIG. 3, line P represents the output pressure of pressure/flow generator 20 over time, and line Q represents the measured tidal volume of the patient's respiration over time. The normal operating pressure of the pressure/ flow generator can be found in time segments 70, 72, 74, and 76, and this may be zero. Alternatively, the standard operating pressure of pressure/flow generator 20 may be slightly positive to flush out $CO_2$ from the patient circuit, e.g., not enough to assist the patient in breathing. As can be seen in the figure by referring to line Q, time periods 70, 72, and 74 demonstrate normal tidal volumes for the patient's respiration, i.e., the patient is breathing in a satisfactory manner. Note that line Q is derived from the readings of sensor 28.

Time period 76, however, illustrates a situation in which satisfactory breath has not been taken by the patient. During this time interval, the patient is considered to be experiencing an apnea or hypopnea. In response to the event occurring in period 76, a back-up breath is supplied to the patient in period 78 by the pressure/flow generator. Specifically, in delivering the timed back-up breath, pressure/flow generator 20 supplies respiratory gases to the patient at a positive pressure (as shown at line P in period 78) exceeding the normal operating pressure of pressure/flow generator 20 of the respiratory system at all other times. This can be done using any conventional pressure/flow control techniques, such by changing the operating speed of the blower in the pressure/flow generator or by manipulating a pressure/flow control valve in the pressure/flow generator. The preset limit that triggers the back-up breath, need not be "time without a breath", the limit could be an indication of tidal volume, or a combination of any respiratory parameter set points, as desired. Further, it is expected that this limit may be varied by the operator using computer 30. The system may provide only one timed back-up breath then return to monitoring the patient's respiratory parameters, or may provide multiple breaths, as desired by the operator.

Pressure/flow generator 20 is effectively off (or at a low pressure) before any episode or event. In an exemplary embodiment, pressure/flow generator 20 returns to this standard operating pressure after an event (with one, two, or other preset number of back-up breaths having been supplied to the patient). Consequently, the ventilator portion of the anesthesia delivery and monitoring system is a passive, back up ventilatory system that assists the patient's respiration only as required.

Figure 4:
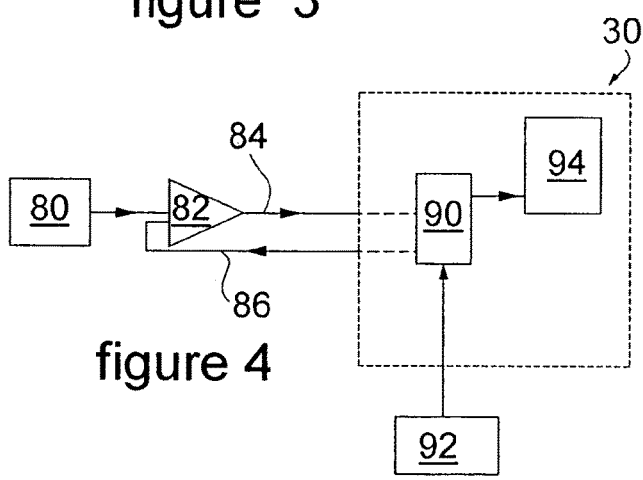
FIG. 4 is a schematic representation of a control system for the physiologic sensor according to the principles of the present invention.

Computer 30 in the present invention serves as an inexpensive, user controlled, physiologic monitor that graphically displays the sensed parameters of patient 12. In an exemplary embodiment of the present invention, each desired physiologic sensor, such as the sensors 28, 40, and 64 discussed above, are coupled to a standard input/output port of computer 30 (including wireless inputs). As shown in FIG. 4, each sensor (generically shown as 80) is coupled through an external amplifier (generically shown as 82) through a link that allows an input signal 84 from the sensor to the computer and a feedback control signal 86 from a controller 90 within computer 30 to amplifier 82. The feedback control signal controls the modification of the output of the physiologic sensor. A user input device 92, such as a keyboard and/or mouse, allows the user to set and modify feedback control signal 86 to control the modification of the output of physiologic sensor 80, such as respiratory sensor 28.

Closed loop feedback control signal 86 controls or drives at least one of a drive current, a drive voltage, a signal gain, a high pass filter point cutoff, a band pass filter range, or a low pass filter point cutoff for modifying the output of sensor 80. Closed loop feedback control signal 86 set by the user gives the user great flexibility in using the desired sensors 80. In clinical use, the sensors 80 will likely have automatic or default settings. In research applications, the desired setting may vary greatly and the present physiologic monitoring system provides a simple, inexpensive tool to the researcher for adjusting these settings.

Figure 5A:
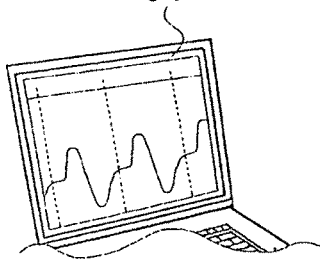
FIGS. 5A-5E are schematic views of various physiologic displays for the PC based physiologic sensors according to the principles of the present invention.
Figure 5B:
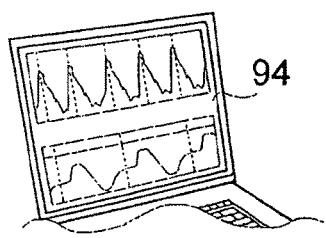
Figure 5C:
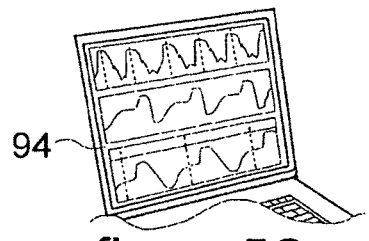
Figure 5D:
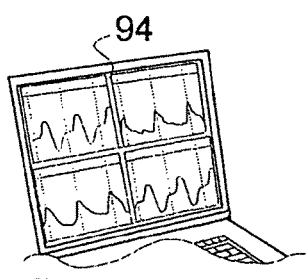
Figure 5E:
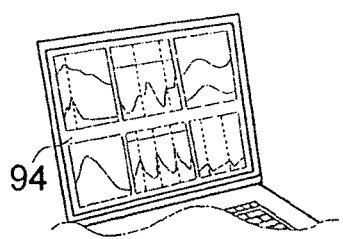

The physiologic monitoring portion of anesthesia delivery and monitoring system 10 and 10' includes a display 94 on computer 30 to display the output or the modified output of sensors 80. Controller 90 identifies each of the sensors that are coupled to the personal computer and sizes a respective display area for each modified output. As shown in FIGS. 5A-5E, a display area of a given modified output associated with one sensor 80 will vary depending upon the specific sensors coupled to the personal computer 30. Specifically, FIG. 5A illustrates an exemplary display area for the output of a sensor 80 when one sensor 80 is attached to computer 30. FIG. 5B illustrates exemplary display areas for the output of two sensors 80 when two sensors 80 are attached to the computer 30. FIG. 5C shows exemplary display areas of three sensors 80. FIG. 5D shows exemplary display areas when four sensors 80 are attached to the computer, and FIG. 5E shows exemplary display areas for six sensors 80.

The display areas in FIGS. 5A-5E are described above as exemplary display areas for several reasons. First, the present invention contemplates providing the user the ability to adjust the size of any window displayed (even electing to eliminate a given display) in a manner familiar to the Windows® operating system. Once the user sets a given display arrangement for a given set of sensors, that display will be the designated display format for those collections of sensors (unless the operator elects to go back to the default settings or the change the display again). Further, the present invention contemplates providing the user with the ability to select an alternative series of displays using any conventional selecting technique, such as via a pull down menu. For example, where there are six sensors attached to the system, the user may elect to display the output of two of the sensors on a first screen (FIG. 5B), the output of three of the sensors on a second screen (FIG. 5C), and the final sensor output on a third screen (FIG. 5A), with the user clicking to toggle or cycle between the given screens. This user defined set up would then become the display setting for this collection of sensors.

Figure 6:
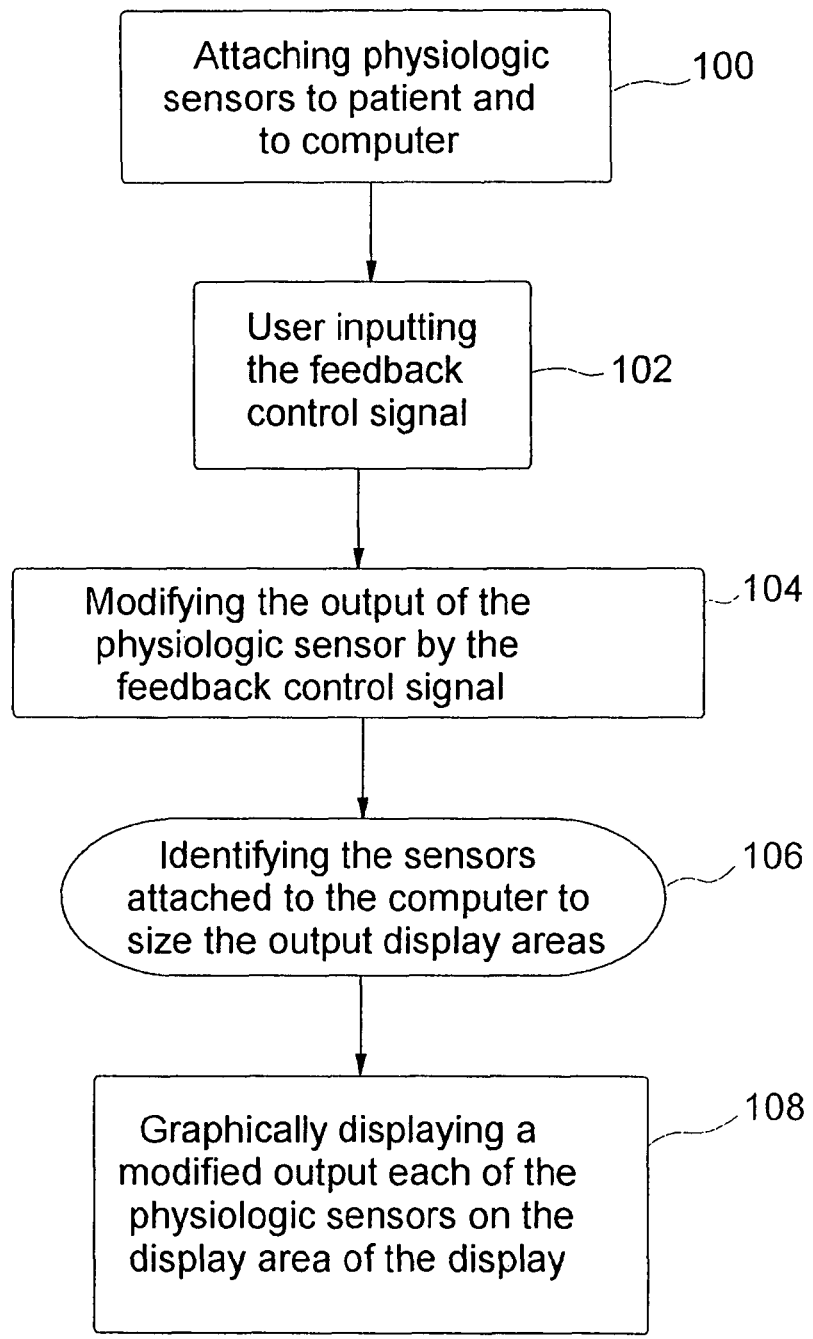
FIG. 6 is a flow chart illustrating a method of monitoring a subject's physiologic parameters on a personal computer according to the principles of the present invention.

As shown in FIG. 6, in using computer 30 as a physiologic monitor, the first step 100 is attaching physiologic sensors 80 to the patient and to the computer, as noted above. Then, in step 102, the user inputs the parameters for the feedback control signals 86 for each sensor 80 (or uses the defaults). At step 104, the output of each of the physiologic sensors 80 is modified by the respective feedback control signal 86. With all of the sensors attached, controller 90 identifies, at step 106, the sensors that are actually attached to the computer to thereby size the output display areas on the display. Finally, computer 30, in step 108, graphically displays a modified output each of the physiologic sensors on the respective display area of display 94.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

DEFINITION OF TERMS USED IN THE SPECIFICATION

The following is a listing of the terms used in the above specification. This listing is intended to supplement and not replace the definition of the terms given above, as understood by those skilled in the art based on the context in which they are presented, but may serve to help clarify the intended meaning of each.

A personal computer within the meaning of this specification is a computer with its own operating system and of software intended for a variety of operations by the user. Examples of personal computers include those commonly referred to as a desk-top computer, a laptop computer, a workstation, or a notebook computer. A personal computer does not include a processor or CPU imbedded within a dedicated piece of equipment.

A physiologic sensor within the meaning of this specification is a sensor that measures a parameter related to a physical characteristic of a living subject, such as a human. The types of physiologic sensors include, for example, blood pressure sensors, blood flow sensors, blood glucose sensors, blood cholesterol sensors, heart sound sensors, EMG sensors, EEG sensors, EKG sensors, EOG sensors, pulse sensors, oxygenation sensors, blood perfusion sensors, respiration sensors (both pressure, flow and rate), temperature sensors, additional blood gas sensors (such as nitrogen partial pressure, carbon dioxide partial pressure, carbon monoxide partial pressure, oxygen partial pressure, and pH level), motion sensors, strain gauges, body position sensors, limb motion sensors and the like. The term respiratory sensors is a subset of physiologic sensors and refers to those sensors measuring physical parameters of a subject indicative of respiration of the subject.

The input/output ports of a personal computer refer to the communications links through which the personal computers send and receive information, which generally include serial ports, parallel ports, wireless links or connectors (such as WI-FI and Bluetooth), and universal serial bus (UBS) ports. In addition, some laptops have expansion slots for PCMCIA standard adaptor cards (Type I and Type II) that also form input/output ports.

The terms sedation anesthesia or sedation level anesthesia within the meaning of this specification refers to a level of a anesthesia below general anesthesia in which a patient is intended to be able to respond to physical stimulus and maintain an airway, also known as a light plane of anesthesia. General anesthesia corresponds to a level of sedation in which a patient does not respond to physical stimulus and, as a result, cannot maintain an airway and breath on their own, also known as a deep plane of anesthesia. These definitions follow the American Society of Anesthesiologists (ASA) definitions.

The term timed back-up breaths within the meaning of this specification refers to the supplying of, through a ventilatory system coupled to the patient, positive pressure assist to a patients breathing in response to a sensed failure of the patient's actual breathing over time or a reduction of the patient's respiratory flow or volume below a given threshold.

The term respiratory gases, within the meaning of this specification, are gases to be breathed by the patient. This includes untreated air, air supplemented with increased oxygen or treated with other medicaments, oxygen, and other gases and combination of gases used for conventional respiratory treatment and care.

What is claimed is:

1. A system for resolving apnea or hypopnea during sedation, the system comprising:
   a respiratory sensor;
   a pressure/flow generator; and
   a computer programmed to perform a method for resolving apnea or hypopnea during sedation, the method including:
      maintaining the pressure/flow generator at a normal operating pressure wherein the normal operating pressure is zero or is not enough to assist the patient in breathing;
      while maintaining the normal operating pressure, using the respiratory sensor, detecting a time interval over which a patient is experiencing apnea or hypopnea; and
      in response to and after detecting the time interval over which the patient is experiencing apnea or hypopnea, operating the pressure/flow generator to provide at least one back-up breath to the patient to assist the patient's breathing at a positive pressure exceeding the normal operating pressure and then returning to the maintaining of the pressure/flow generator at the normal operating pressure.

2. The system of claim 1 comprising a passive back-up ventilator system in which the maintaining of the pressure/flow generator at the normal operating pressure comprises keeping the pressure/flow generator off except when operating the pressure/flow generator to provide the at least one back-up breath to the patient.

3. The system of claim 1 further comprising:
   an anesthesia gas supply input conduit; and
   a $CO_2$/anesthesia scrubber;
   wherein the pressure/flow generator, the anesthesia gas supply input conduit, and the $CO_2$/anesthesia scrubber are configured to operate as a system for supplying sedation anesthesia to the patient.

4. The system of claim 1 further comprising an intravenous anesthesia supply system.

5. The system of claim 1 wherein the pressure/flow generator comprises a blower.

6. The system of claim 1 further comprising a nasal mask, nasal/oral mask, or nasal cannula operatively coupled to deliver the at least one back-up breath from the pressure/flow generator to the patient.

7. The system of claim 1 wherein the respiratory sensor comprises a pressure sensor or flow sensor.

8. The system of claim 1 wherein the respiratory sensor is configured to measure tidal volume of the patient's respiration over time and the time interval over which the patient is experiencing apnea or hypopnea is detected as a time interval without a breath as indicated by the measured tidal volume.

9. The system of claim 1 wherein, in response to and after detecting the time interval over which the patient is experiencing apnea or hypopnea, the pressure/flow generator is operated to provide a single back-up breath to the patient at the positive pressure exceeding the normal operating pressure and then returns to the maintaining of the pressure/flow generator at the normal operating pressure.

10. The system of claim 1 wherein the computer is a personal computer with its own operating system.

11. A method for resolving apnea or hypopnea during sedation, the method comprising:
   sedating a patient at a sedation level in which the airway is not protected and breathing is not assisted;
   with the patient sedated, maintaining a normal operating pressure delivered to the patient by a pressure/flow generator wherein the normal operating pressure is zero or is not enough to assist the patient in breathing; and
   with the patient sedated and while maintaining the normal operating pressure delivered to the patient, detecting a time interval over which the patient is experiencing apnea or hypopnea using a respiratory sensor and, in response to and after detecting the time interval over which the patient is experiencing apnea or hypopnea, operating the pressure/flow generator to provide at least one back-up breath to the patient to assist the patient's breathing at a positive pressure exceeding the normal operating pressure and then returning to the normal operating pressure delivered to the patient by the pressure/flow generator;

wherein the maintaining of the normal operating pressure, the detecting of the time interval over which the patient is experiencing apnea or hypopnea, and the operating of the pressure/flow generator to provide the at least one back-up breath to the patient are performed by a computer.

12. The method of claim 11 wherein the maintaining of the normal operating pressure comprises keeping the pressure/flow generator off except when operating the pressure/flow generator to provide the at least one back-up breath to the patient.

13. The method of claim 11 wherein sedating the patient includes delivering anesthesia to the patient using the pressure/flow generator maintained at the normal operating pressure delivered to the patient.

14. The method of claim 11 wherein sedating the patient includes delivering anesthesia to the patient using an intravenous anesthesia supply system or a needle and syringe injection.

15. The method of claim 11 wherein:
the normal operating pressure is delivered to the patient by the pressure/flow generator via a nasal mask, nasal/oral mask, or nasal cannula;
and the at least one back-up breath is provided to the patient via the nasal mask, nasal/oral mask, or nasal cannula.

16. The method of claim 11 wherein the time interval over which the patient is experiencing apnea or hypopnea is detected as a time interval without a breath being detected using the respiratory sensor.

17. The method of claim 11 wherein, in response to and after detecting the time interval over which the patient is experiencing apnea or hypopnea, the pressure/flow generator is operated to provide a single back-up breath to the patient at the positive pressure and then returns to the normal operating pressure delivered to the patient by the pressure/flow generator.

18. A system for resolving apnea or hypopnea during sedation, the system comprising:
a respiratory sensor;
a blower; and
a computer programmed to perform a method for resolving apnea or hypopnea during sedation, the method including:
using the respiratory sensor, detecting a time interval over which a patient is experiencing apnea or hypopnea;
in response to and after detecting the time interval over which the patient is experiencing apnea or hypopnea, operating the blower to provide at least one back-up breath to the patient to assist the patient's breathing; and
keeping the blower off except when operated to provide the at least one back-up breath to the patient.

19. The system of claim 18 wherein the time interval over which the patient is experiencing apnea or hypopnea is detected as a time interval without a breath as indicated by the measured tidal volume.

20. The system of claim 19 wherein, in response to and after detecting the time interval over which the patient is experiencing apnea or hypopnea, the blower is operated to provide a single back-up breath to the patient.

21. A system for resolving apnea or hypopnea during sedation, the system comprising:
a respiratory sensor;
a pressure/flow generator; and
a computer programmed to perform a method for resolving apnea or hypopnea during sedation, the method including:
maintaining the pressure/flow generator at a normal operating pressure wherein the normal operating pressure is zero or is not enough to assist the patient in breathing;
using the respiratory sensor, detecting a time interval over which a patient is experiencing apnea or hypopnea; and
in response to and after detecting the time interval over which the patient is experiencing apnea or hypopnea, operating the pressure/flow generator to provide at least one back-up breath to the patient to assist the patient's breathing at a positive pressure exceeding the normal operating pressure and then returning to the maintaining of the pressure/flow generator at the normal operating pressure; and
a passive back-up ventilator system in which the maintaining of the pressure/flow generator at the normal operating pressure comprises keeping the pressure/flow generator off except when operating the pressure/flow generator to provide the at least one back-up breath to the patient.

* * * * *